United States Patent
Burgi

(10) Patent No.: US 8,585,709 B2
(45) Date of Patent: Nov. 19, 2013

(54) STRAIGHT CUP IMPACTOR WITH LEVER ARM

(75) Inventor: Jonas Burgi, Moutier (CH)

(73) Assignee: Greatbatch Medical S.A., Orvin (CH)

( * ) Notice: Subject to any disclaimer, the term of this patent is extended or adjusted under 35 U.S.C. 154(b) by 199 days.

(21) Appl. No.: 13/351,302

(22) Filed: Jan. 17, 2012

(65) Prior Publication Data

US 2012/0184965 A1    Jul. 19, 2012

Related U.S. Application Data

(60) Provisional application No. 61/433,383, filed on Jan. 17, 2011.

(51) Int. Cl.
*A61B 17/88* (2006.01)
*A61B 17/92* (2006.01)

(52) U.S. Cl.
USPC .............................................. 606/91; 606/99

(58) Field of Classification Search
USPC ................... 606/86 R, 91, 99; 623/22.12
See application file for complete search history.

(56) References Cited

U.S. PATENT DOCUMENTS

| | | | |
|---|---|---|---|
| 1,942,422 A | 6/1931 | Hanna | |
| 4,305,394 A | 12/1981 | Bertuch, Jr. | |
| D272,648 S | 2/1984 | Bolesky et al. | |
| D273,806 S | 5/1984 | Bolesky et al. | |
| 4,475,549 A | 10/1984 | Oh | |
| 4,520,511 A | 6/1985 | Gianezio et al. | |
| 4,528,980 A | 7/1985 | Kenna | |
| 4,587,964 A | 5/1986 | Walker et al. | |
| 4,632,111 A | 12/1986 | Roche | |
| 4,716,894 A | 1/1988 | Lazzeri et al. | |
| 4,765,328 A | 8/1988 | Keller et al. | |
| 4,904,267 A | 2/1990 | Bruce et al. | |
| 4,919,679 A | 4/1990 | Averill et al. | |
| 4,921,493 A | 5/1990 | Webb, Jr. et al. | |
| 5,019,105 A | 5/1991 | Wiley | |

(Continued)

FOREIGN PATENT DOCUMENTS

| | | |
|---|---|---|
| DE | 10250390 | 5/2004 |
| EP | 0453694 | 10/1991 |

(Continued)

OTHER PUBLICATIONS

European Search Report dated Apr. 15, 2011.

(Continued)

*Primary Examiner* — Nicholas Woodall
*Assistant Examiner* — Larry E Waggle, Jr.
(74) *Attorney, Agent, or Firm* — Steven W. Winn

(57) ABSTRACT

An orthopedic impactor device for positioning an orthopedic prosthetic cup implant during a hip replacement surgery is described. The impactor is designed with a "one piece" elongated body portion, having a distal prosthetic cup engagement portion which is separated from a proximal strike plate by an annular sidewall. A handle portion is positioned circumferentially around the annular sidewall of the elongated body in a slidable relationship along a longitudinal axis. A rod, connectable to an orthopedic prosthetic cup, is positioned within a cavity of the body and connected to the proximal ring. A lever arm having a distal wedge portion is pivotally connected to the handle portion such that when the lever arm is pivoted towards the annular sidewall of the handle portion, the distal end of the rod moves within the body cavity.

26 Claims, 12 Drawing Sheets

(56) References Cited

U.S. PATENT DOCUMENTS

| | | |
|---|---|---|
| 5,037,424 A | 8/1991 | Aboczsky |
| 5,061,270 A | 10/1991 | Aboczky |
| 5,062,854 A | 11/1991 | Noble et al. |
| 5,089,003 A | 2/1992 | Fallin et al. |
| 5,116,339 A | 5/1992 | Glock |
| 5,124,106 A | 6/1992 | Morr et al. |
| 5,133,766 A | 7/1992 | Halpern |
| 5,169,399 A | 12/1992 | Ryland et al. |
| 5,190,549 A | 3/1993 | Miller et al. |
| 5,234,432 A | 8/1993 | Brown |
| 5,261,915 A | 11/1993 | Durlacher et al. |
| 5,324,293 A | 6/1994 | Rehmann |
| 5,342,362 A | 8/1994 | Kenyon et al. |
| 5,364,403 A | 11/1994 | Petersen et al. |
| 5,417,696 A | 5/1995 | Kashuba et al. |
| 5,443,471 A | 8/1995 | Swajger |
| 5,454,815 A | 10/1995 | Geisser et al. |
| 5,485,887 A | 1/1996 | Mandanis |
| 5,540,697 A | 7/1996 | Rehmann et al. |
| 5,584,837 A | 12/1996 | Petersen |
| 5,658,294 A | 8/1997 | Sederholm |
| 5,665,091 A | 9/1997 | Noble et al. |
| 5,683,399 A | 11/1997 | Jones |
| 5,707,374 A | 1/1998 | Schmidt |
| 5,720,750 A | 2/1998 | Koller et al. |
| 5,863,295 A | 1/1999 | Averill et al. |
| 5,913,860 A | 6/1999 | Scholl |
| 5,976,148 A | 11/1999 | Charpenet et al. |
| 5,993,455 A | 11/1999 | Noble |
| 6,063,124 A | 5/2000 | Amstutz |
| 6,120,508 A | 9/2000 | Grunig et al. |
| 6,197,065 B1 | 3/2001 | Martin et al. |
| 6,432,141 B1 | 8/2002 | Stocks et al. |
| 6,451,058 B2 | 9/2002 | Tuke et al. |
| 6,626,913 B1 | 9/2003 | McKinnon et al. |
| 6,663,636 B1 | 12/2003 | Lin |
| 6,811,569 B1 | 11/2004 | Afriat et al. |
| 7,192,449 B1 | 3/2007 | McQueen et al. |
| 7,335,207 B1 | 2/2008 | Smith |
| 7,341,593 B2 | 3/2008 | Auxepaules et al. |
| 7,396,357 B2 | 7/2008 | Tornier et al. |
| 7,585,301 B2 | 9/2009 | Santarella et al. |
| 7,591,821 B2 | 9/2009 | Kelman |
| 7,604,667 B2 | 10/2009 | DeSmet et al. |
| 7,621,921 B2 | 11/2009 | Parker |
| 7,922,726 B2 | 4/2011 | White |
| 2001/0051830 A1 | 12/2001 | Tuke et al. |
| 2002/0004660 A1 | 1/2002 | Henniges et al. |
| 2002/0116007 A1 | 8/2002 | Lewis |
| 2002/0177854 A1 | 11/2002 | Tuke et al. |
| 2002/0193797 A1 | 12/2002 | Johnson et al. |
| 2003/0009234 A1 | 1/2003 | Treacy et al. |
| 2003/0050645 A1 | 3/2003 | Parker et al. |
| 2003/0083668 A1 | 5/2003 | Rogers et al. |
| 2003/0088316 A1 | 5/2003 | Ganjianpour |
| 2003/0187512 A1 | 10/2003 | Frederick et al. |
| 2003/0220698 A1 | 11/2003 | Mears et al. |
| 2003/0229356 A1 | 12/2003 | Dye |
| 2004/0215200 A1 | 10/2004 | Tornier et al. |
| 2005/0038443 A1 | 2/2005 | Hedley et al. |
| 2005/0075736 A1 | 4/2005 | Collazo |
| 2005/0137603 A1 | 6/2005 | Belew et al. |
| 2005/0171548 A1 | 8/2005 | Kelman |
| 2005/0187562 A1 | 8/2005 | Grimm et al. |
| 2005/0222572 A1 | 10/2005 | Chana |
| 2005/0228395 A1 | 10/2005 | Auxepaules et al. |
| 2005/0234462 A1 | 10/2005 | Hershberger |
| 2005/0246031 A1 | 11/2005 | Frederick et al. |
| 2006/0052780 A1 | 3/2006 | Errico et al. |
| 2006/0149285 A1 | 7/2006 | Burgi et al. |
| 2007/0156155 A1 | 7/2007 | Parker |
| 2007/0167952 A1 | 7/2007 | Burgi et al. |
| 2007/0225725 A1 | 9/2007 | Heavener et al. |
| 2007/0270783 A1 | 11/2007 | Zumsteg et al. |
| 2007/0288096 A1 | 12/2007 | Surma |
| 2007/0293869 A1 | 12/2007 | Conte et al. |
| 2008/0004628 A1 | 1/2008 | White |
| 2008/0021481 A1 | 1/2008 | Burgi |
| 2008/0033444 A1 | 2/2008 | Bastian et al. |
| 2008/0077249 A1 | 3/2008 | Gradel |
| 2008/0146969 A1 | 6/2008 | Kurtz |
| 2008/0154261 A1 | 6/2008 | Burgi |
| 2008/0243127 A1 | 10/2008 | Lang et al. |
| 2008/0255565 A1 | 10/2008 | Fletcher |
| 2008/0255568 A1 | 10/2008 | Tornier et al. |
| 2008/0262503 A1 | 10/2008 | Muller |
| 2008/0275450 A1 | 11/2008 | Myers et al. |
| 2009/0112214 A1 | 4/2009 | Philippon et al. |
| 2009/0182334 A1 | 7/2009 | Brehm |
| 2009/0192515 A1 | 7/2009 | Lechot et al. |
| 2009/0240256 A1 | 9/2009 | Smith |
| 2009/0281545 A1 | 11/2009 | Stubbs |

FOREIGN PATENT DOCUMENTS

| | | | |
|---|---|---|---|
| EP | 0470912 | 12/1992 | |
| EP | 0535973 | 4/1993 | |
| EP | 357302 | 7/1994 | |
| EP | 638299 | 2/1995 | |
| EP | 1308140 | 5/2003 | |
| EP | 1190687 | 7/2004 | |
| EP | 1438936 | 7/2004 | |
| EP | 1447058 | 8/2004 | |
| WO | 9511641 | 5/1995 | |
| WO | 0012832 | 3/2000 | |
| WO | 0106964 | 2/2001 | |
| WO | WO 2004010882 A1 * | 2/2004 | ............ A61B 17/92 |
| WO | 2005044153 | 5/2005 | |
| WO | 2006061708 | 6/2006 | |
| WO | 2007098549 | 9/2007 | |
| WO | 2008128282 | 10/2008 | |
| WO | 2009136284 | 11/2009 | |

OTHER PUBLICATIONS

European Search Report dated Feb. 28, 2012.

* cited by examiner

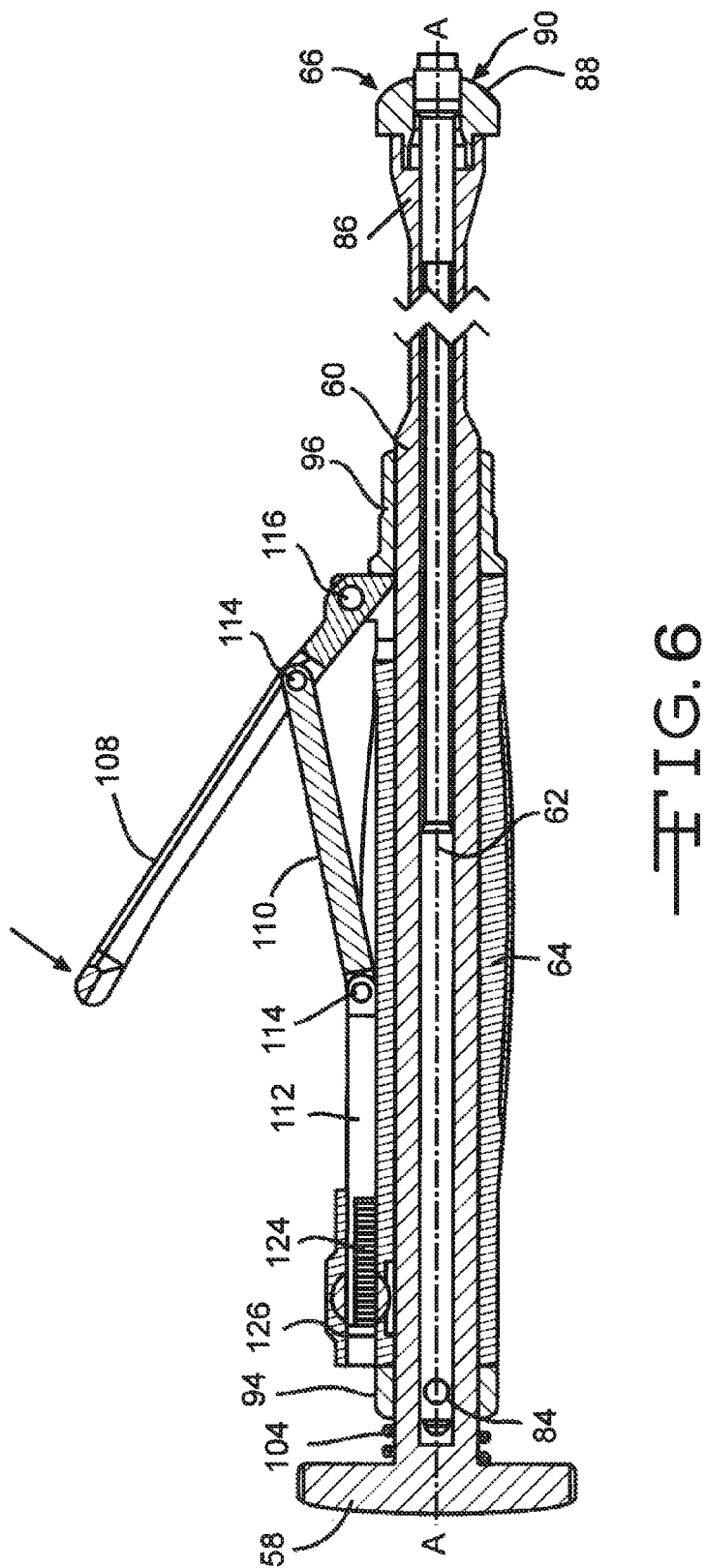

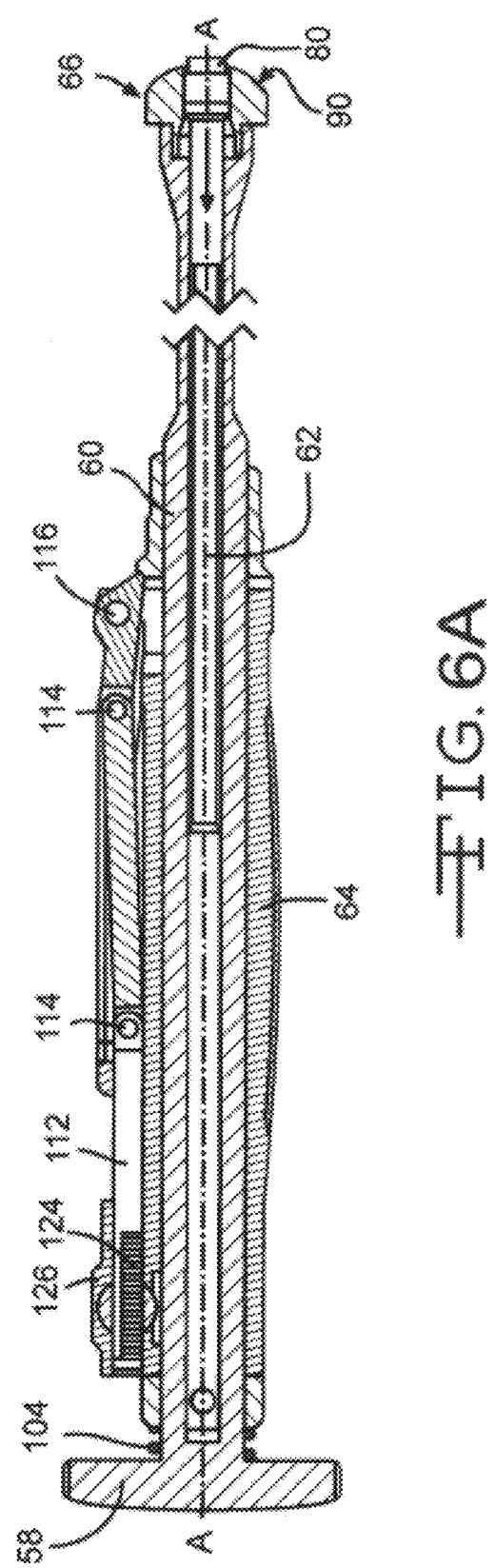

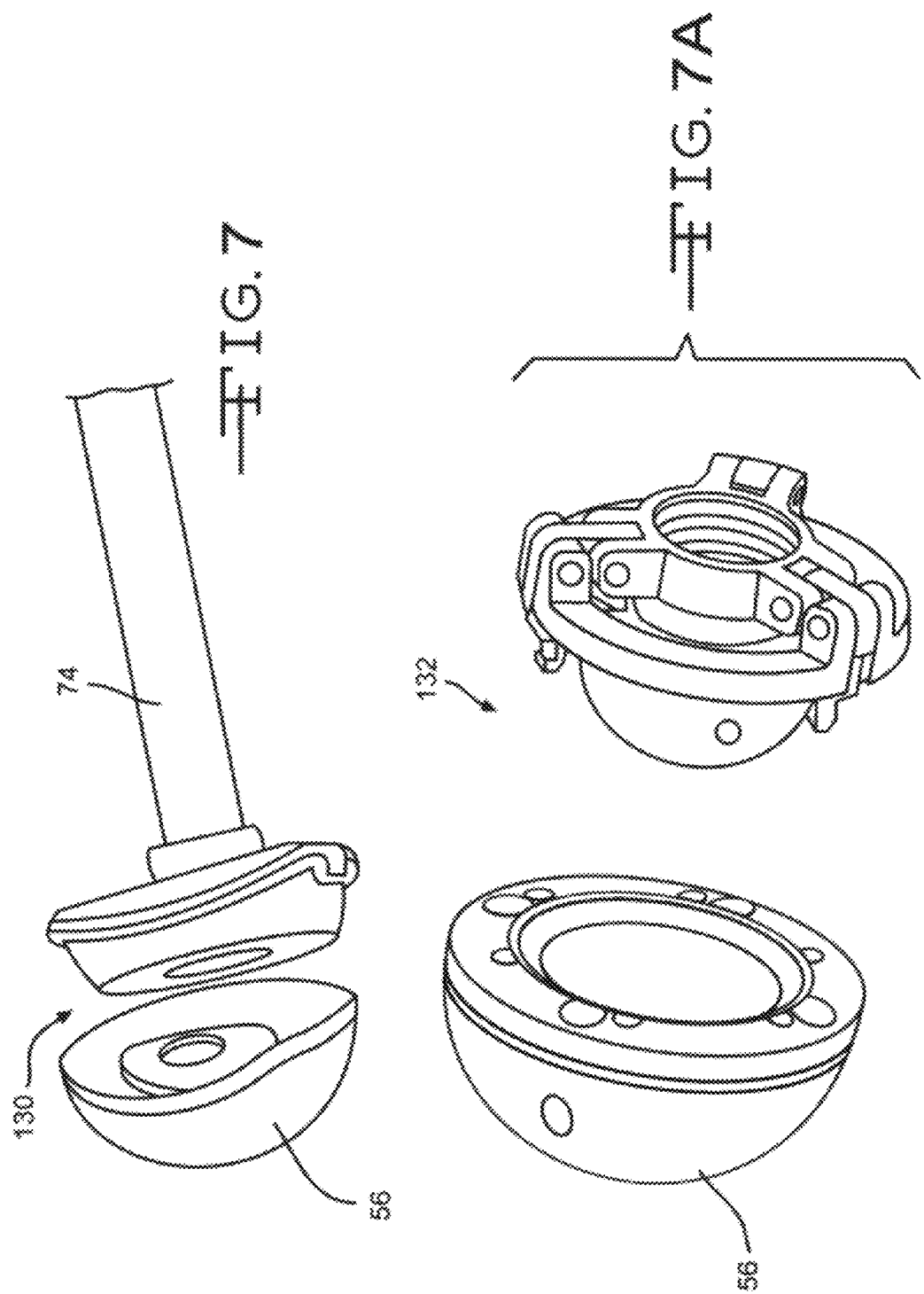

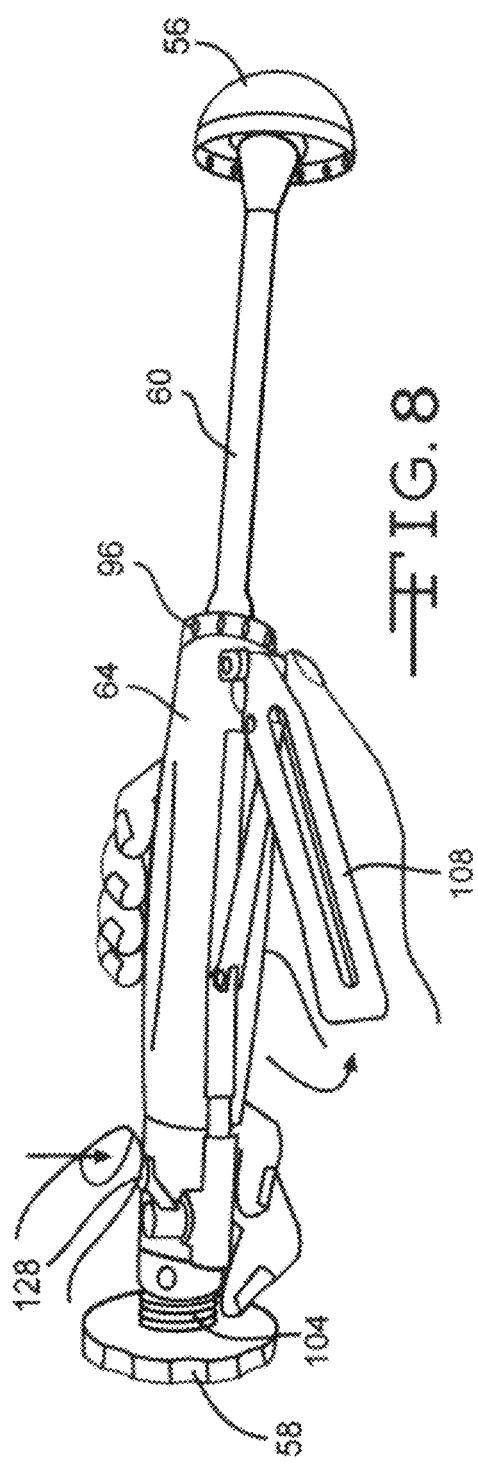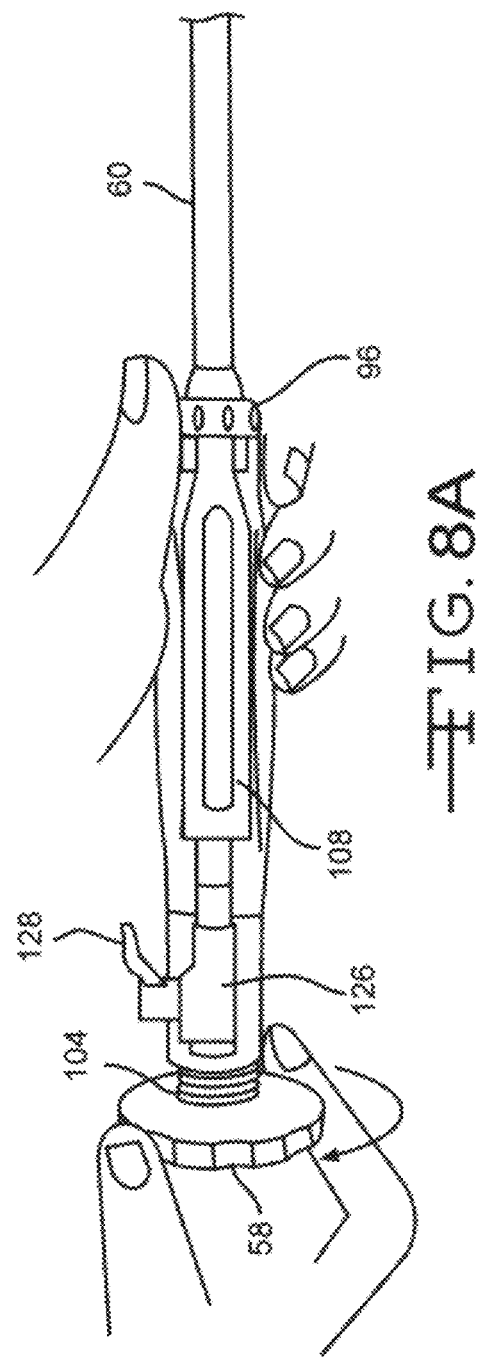

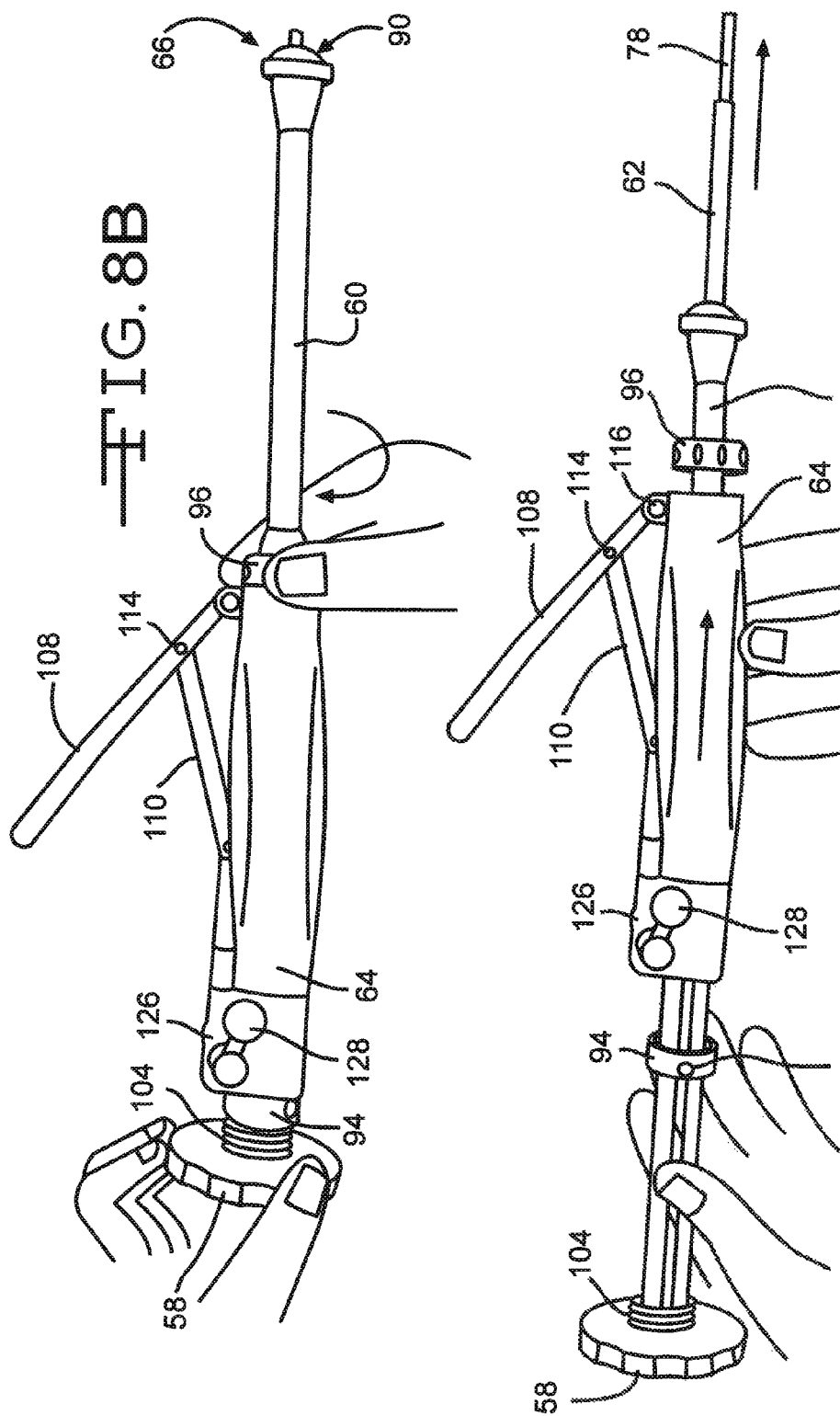

STRAIGHT CUP IMPACTOR WITH LEVER ARM

CROSS-REFERENCE TO RELATED APPLICATIONS

This application claims priority from U.S. Provisional Patent Application Ser. No. 61/433,383, filed Jan. 17, 2011.

FIELD OF THE INVENTION

The invention relates to surgical tools for aiding a surgeon installing an orthopedic prosthesis. More specifically, the invention relates to an orthopedic cup impactor for positioning an acetabular cup prosthesis within the body.

BACKGROUND OF THE INVENTION

A total hip replacement is a reconstructive surgical procedure typically performed by an orthopedic surgeon. A total hip replacement involves the placement of an acetabular cup within, a patient's acetabular socket, and the replacement of the patient's femoral neck with a prosthesis which terminates in a ball specifically designed to be positioned in the acetabular cup. Other surgical procedures may require the application of an acetabular cup or other device applied to a patient.

For example, during such acetabular cup procedures, the patient's acetabular socket is reamed out by the surgeon so as to create an enlarged recess to receive the acetabular cup. After the acetabular socket has been reamed, the cup is inserted into the recess and adjusted as necessary to the proper angular orientation. Once deployed, the cup provides a new socket and lining for the patient's acetabulum.

Insertion and placement of the cup by the surgeon is effected either by hand or by use of a hand tool that grips the cup. Once the cup is properly positioned in the acetabulum, the cup can be fixed in the desired location by various means such as bone screws, medically acceptable adhesives, or combinations thereof. In many instances, the fixation means include passing bone screws through the cup and into pre-drilled screw holes in the pelvic bone. The bone screws, which are optional, serve to hold the acetabular cup in the acetabulum until bone ingrowth provides permanent fixation.

In one acceptable medical method, the cup is properly positioned in the acetabulum by implantation. One conventional implantation method is, after obtaining proper alignment, to impact an acetabular cup into place. While impacting the acetabular cup, the surgeon listens for a change in pitch as the cup seats down. The surgeon then probes screw holes to determine if a gap between the cup and the bone is present. If a gap is present, the surgeon further impacts the cup into the acetabulum.

FIGS. 1 and 2 illustrate a conventional spindle-type orthopedic surgical impactor 10. As shown, this prior art impactor 10 has a strike plate 12 that is integrally connected to a proximal end 16 of the impactor body 14. Extending from the strike plate 12 and positioned over a proximal area of the body portion 14 is a fixed handle 18. The fixed handle 18 has a length that allows a surgeon to hold the impactor 10, in one embodiment with one hand, and in an alternative embodiment with two hands. Whatever the fixed handle's 18 length, extending there from on the body 14, is an impactor thread section 20. At the body portion's distal end 22 is a tool thread section 24.

The tool thread section 24 threadingly interconnects to a surgical implant device (a.k.a., medical attachment) 26, for example, and not limited to, an acetabular cup, through a threaded aperture 28 (FIG. 2). That means the implant device 26 is directly connected to the body 14 and the strike plate 12. To ensure the surgical implant device 26 is properly secured to the tool thread section 24, the prior art device 10 uses rotate handle device 30 (FIG. 2A).

The rotate handle 30 is positioned in the spacing between the tool thread section 24 and the impactor thread section 20. At its proximal end, the rotate handle device 30 has a rotating threaded section 32 and at its distal end, an implant support 34. The rotating threaded section 32 has threads that mate with the impactor thread section 20. When the rotating threaded section 32 is rotated clockwise (illustrated by arrow 36 at FIG. 1), (a) the rotating threaded section 32 pushes (illustrated by arrow 38) the rotate handle 30 and the implant support surface 34 toward the surgical implant device's interior surface 40 (FIG. 2); and (b) simultaneously, the rotating threaded section 32, through a conventional lock-nut structure, rotates the surgical implant device 26 counter-clockwise (arrow 42 at FIG. 1). This movement results in the surgical implant 26 being pushed toward the implant support 34. Collectively, the clock-wise rotating threaded section 32 is designed to securely position the surgical implant 26 against the implant support 34 to inhibit dislodging of the surgical implant device 26 from the spindle-type tool holder 10 when the surgeon impacts the tool holder.

However, when the surgeon impacts the strike plate 12 there is a possibility that the surgical implant 26 can disconnect from the impactor 10. This could occur when the threaded section 24 or the implant's 26 corresponding threaded section 28 is damaged from impaction force. Accordingly, what is needed is a firm fixation of the surgical implant 26 during impaction that provides minimal damage to the implant's 26 threads 28. That desired product is achieved with the present invention.

SUMMARY OF THE INVENTION

The cup impactor of the present invention comprises an elongated body with respective distal and proximal ends. The elongated body is constructed with a strike plate residing at the body's proximal end, and an impactor cup engagement portion located at the body's opposing distal end. The elongated body is constructed of a one-piece design. The elongated body is designed such that the strike plate fluidly extends from the proximal end portion through a body length portion to the impactor cup engagement portion at the distal end portion.

A connection rod, having respective proximal and distal rod ends, is positioned within an elongated cavity of the body. The distal end of the connection rod is constructed with a threaded end that is designed to threadably attach to a threaded aperture of a prosthetic orthopedic cup. The proximal end portion of the connection rod resides within the body cavity such that the rod's proximal end does not contact the inside wall surface of the body.

In an embodiment of the impactor of the present invention, the proximal end portion is connected to a ring that circumferentially extends around an exterior surface of the annular sidewall of the body. The ring is designed such that it is in a slidable relationship along the elongated body. A rod connection pin extends perpendicularly through the proximal end of the connection rod. The opposing rod ends are positioned such that they extend through opposing slots of the annular sidewall of the body, connecting with the ring's annular sidewall. Thus, contact of the proximal end of the connection rod with the inside cavity wall of the body is prevented.

Therefore, because the proximal end of the connection rod is prevented from contacting the inner surface of the proximal end of the cavity of the body, the possibility that impaction forces are transferred to the surgical implant through the connection rod, are reduced. As a result, the possibly of causing damage to the cup implant, particularly the prosthetic cup's connection mechanism, is reduced.

The cup impactor of the present invention further comprises a lever arm subassembly that actuates movement of the connection rod and thus movement of the prosthetic cup. The lever arm subassembly is designed such that when the lever arm is moved in a pivotable manner in a downward direction, i.e., closer to the external surface of the body's annular sidewall, the connection rod is retracted into the cavity of the body. Since the distal end of the connection rod is preferably connected to the prosthetic cup, retraction of the rod within the body pulls implant cup in a proximal direction, closer to the cup engaging portion of the impactor. Likewise, when the lever arm is pivoted away from the external surface of the annular sidewall of the body, the connection rod and therefore the prosthetic cup, move distally away from the distal end of the impactor.

In a further embodiment, the lever arm subassembly comprises a releasable ratchet locking mechanism. The locking mechanism enables the prosthetic cup to be locked in a multitude of positions with respect to the impactor. The locking mechanism release lever further allows for quick release and disassembly of the prosthetic cup from the impactor.

In yet another embodiment of the impactor of the present invention, the one-piece construction of the impactor body portion of the impactor minimizes the possibility that the associated components of the impactor are misplaced. The impactor is constructed such that its components are either connected to or contained within the elongated body portion, thereby preventing displacement of the components from the impactor.

BRIEF DESCRIPTION OF THE DRAWINGS

FIG. 2A illustrates the prior art handle device 30 of FIG.

FIGS. 6-6B illustrate cross-sectional views of the locking mechanism subassembly connecting a prosthetic cup to the impactor shown in FIG. 3.

FIGS. 7 and 7A illustrate perspective views of alternate embodiments of prosthetic cup to impactor engagement mechanisms.

FIGS. 8-8D are perspective views illustrating an embodiment of a disassembly process of the present invention.

DETAILED DESCRIPTION OF THE INVENTION

Figure 1:
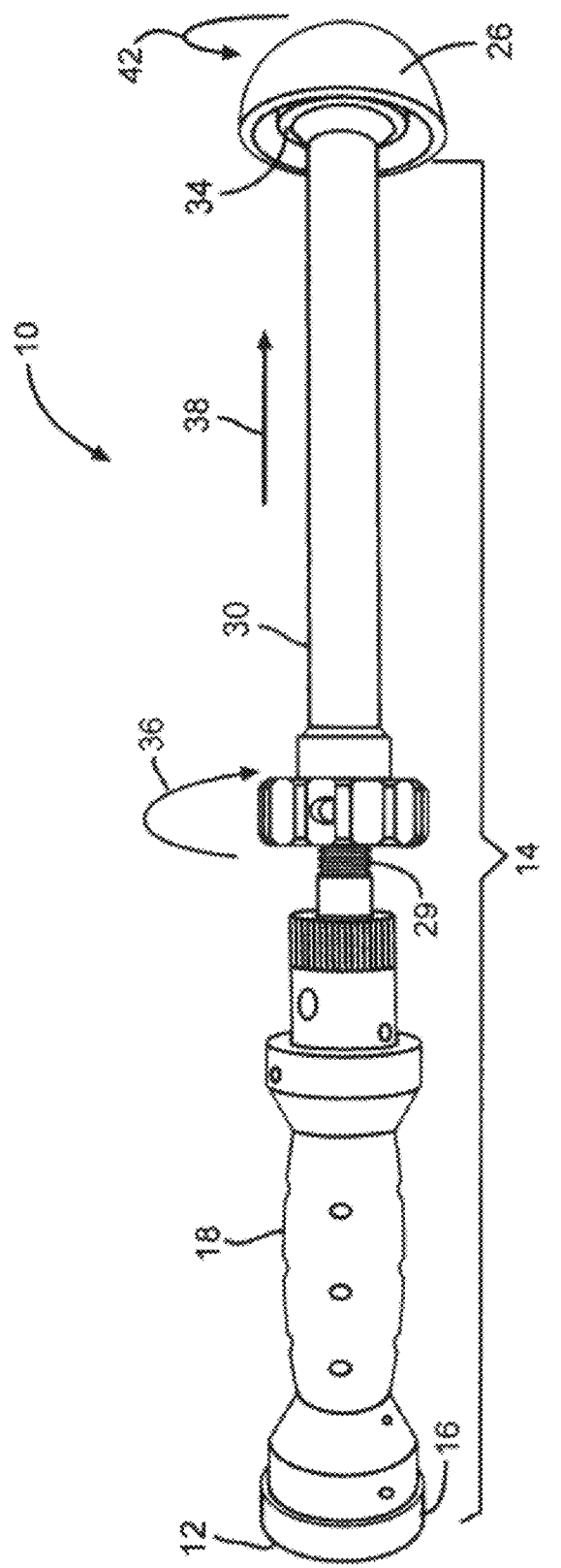
FIG. 1 illustrates an embodiment of a prior art orthopedic impactor.
Figure 2:
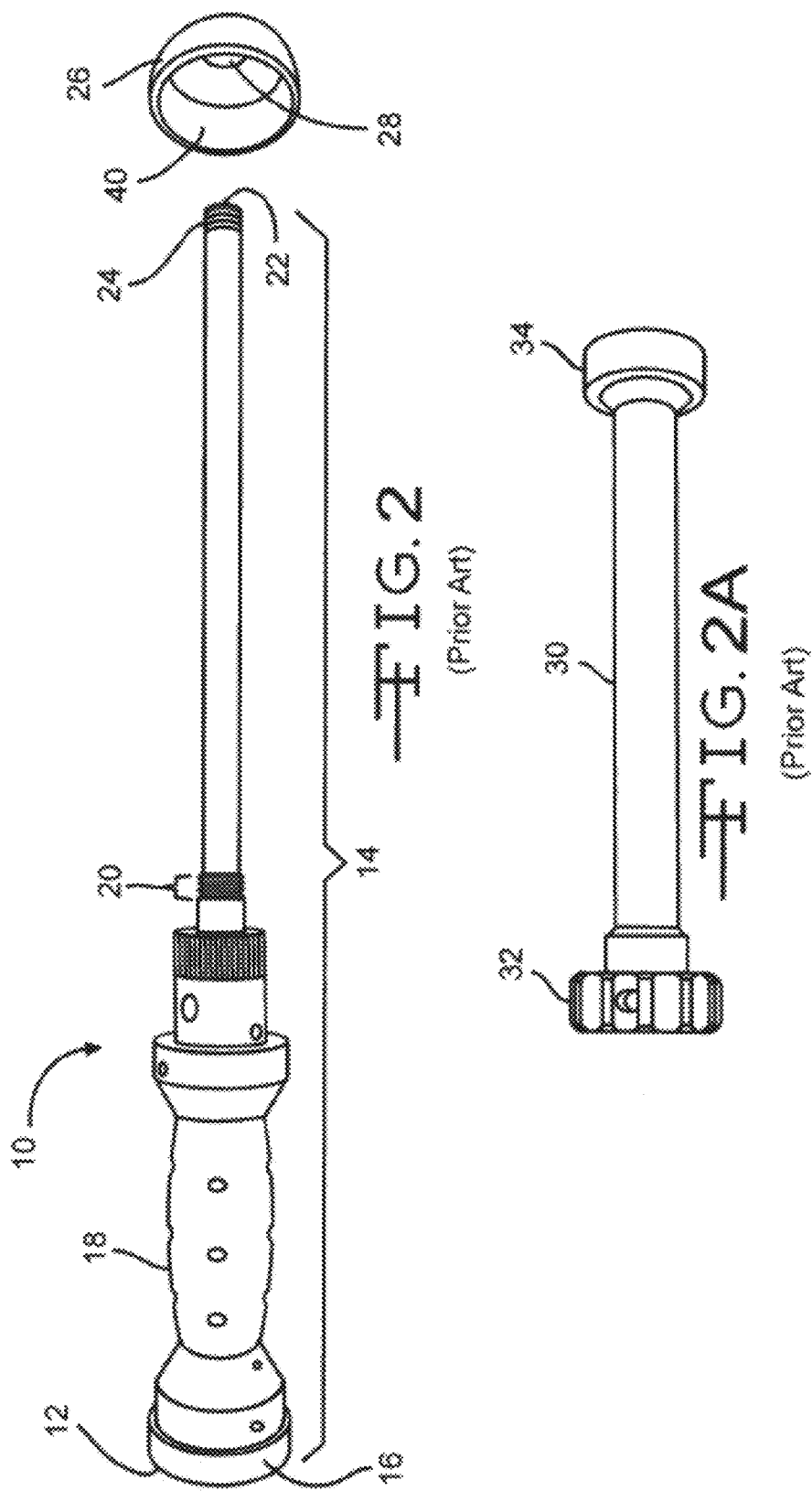
FIG. 2 shows the handle 18 and connected body portion 14 of the prior art impactor shown in FIG. 1.
Figure 3:
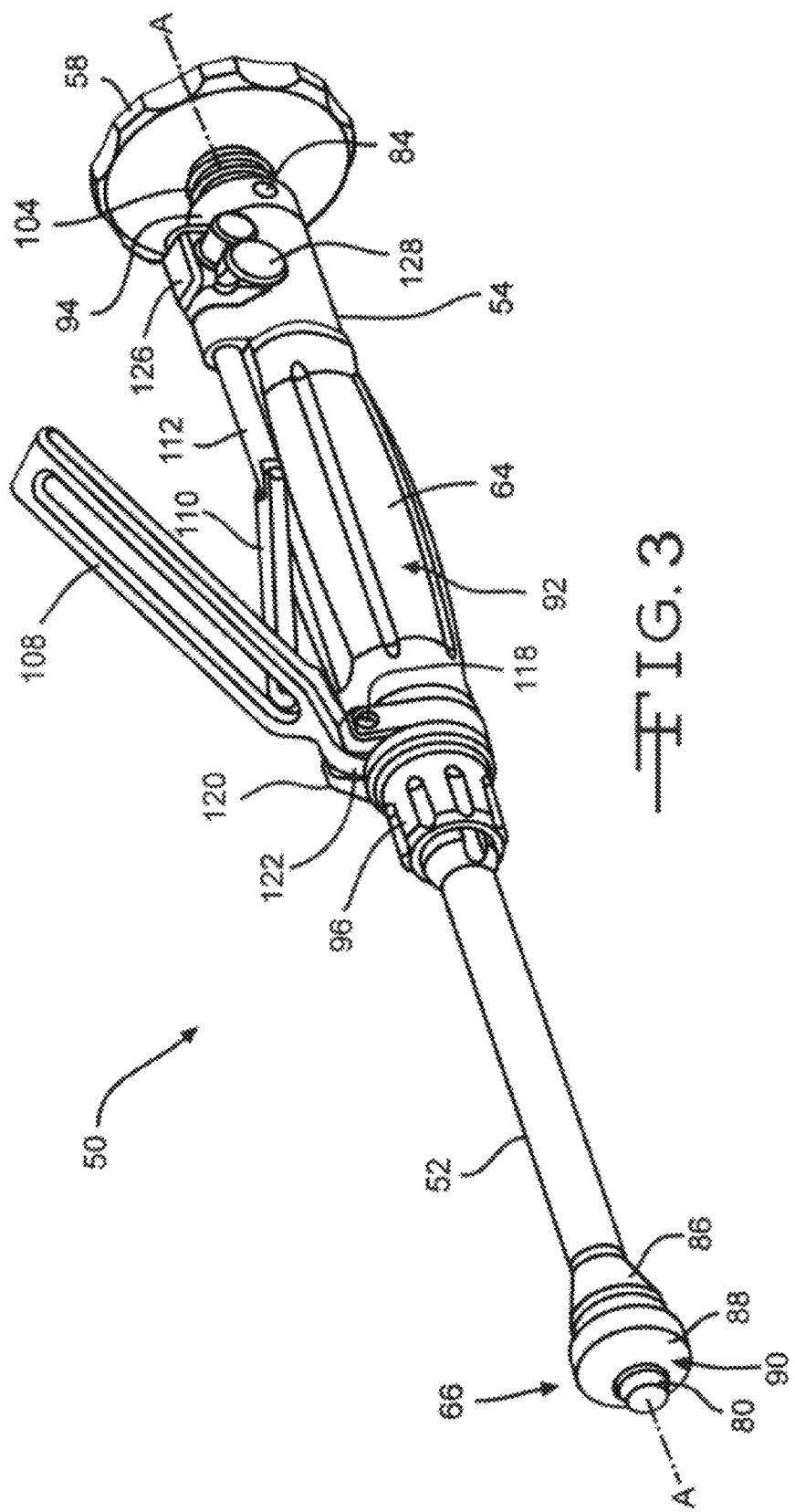
FIG. 3 illustrates a perspective view of the spindle-type orthopedic impactor of the present invention.

Now turning to the figures, FIGS. 3-5, 6-6B and 8-8D illustrate a spindle-type orthopedic impactor 50 of the present invention. As shown in FIG. 3, the orthopedic impactor 50 comprises a distal end portion 52 spaced from a proximal end portion 54 with a length portion residing therebetween. An orthopedic prosthetic cup 56 is designed to be positioned at the distal end of the impactor 50 and a strike plate 58 resides at the proximal end of the impactor 50.

More specifically, as illustrated in FIGS. 4, 6-6B, 8C and 8D, the impactor 50 of the present invention comprises an elongated body portion 60, a connection rod 62 positioned within the body 60, and a handle portion 64 residing circumferentially around the body 60. As shown, the body portion 60 extends lengthwise along longitudinal axis A-A. In a preferred embodiment, the body portion 60 is of a "one-piece" construction in that the strike plate 58, located at the proximal end of the impactor 50, and a prosthetic cup engagement portion 66, located at the distal end of the impactor 50 are fluidly connected in one-piece.

The elongated body portion 60 is constructed with a curved outer sidewall 68. More preferably, the elongated body portion 60 is constructed with an annular sidewall 68 with an outer diameter ranging from about 1 cm to about 5 cm. Although it is preferred that the elongated body is constructed with an outer circular cross-section, the body 60 may be constructed of a multitude of cross-sectional shapes that include but are not limited to a rectangle, a square, a triangle, a hexagon, or an oval.

The elongated body portion 60 has a length that ranges from about 5 cm to about 50 cm and more preferably from about 10 cm to about 25 cm. The body portion 60 may be constructed of either a polymer or metallic material. Specifically, the body portion 60 may be constructed from polymers comprising polyether ether ketone (PEEK), acryloyl b-alanine (ABA), acryloyl b-alanine tri-block copolymers and the like. In addition, the body portion may be constructed from metals comprising aluminum, stainless steel, cobalt nickel alloys, highly alloyed ferritic stainless steel containing molybdenum and chromium, and nickel chromium- and molybdenum-containing alloys and the like.

Figure 4:
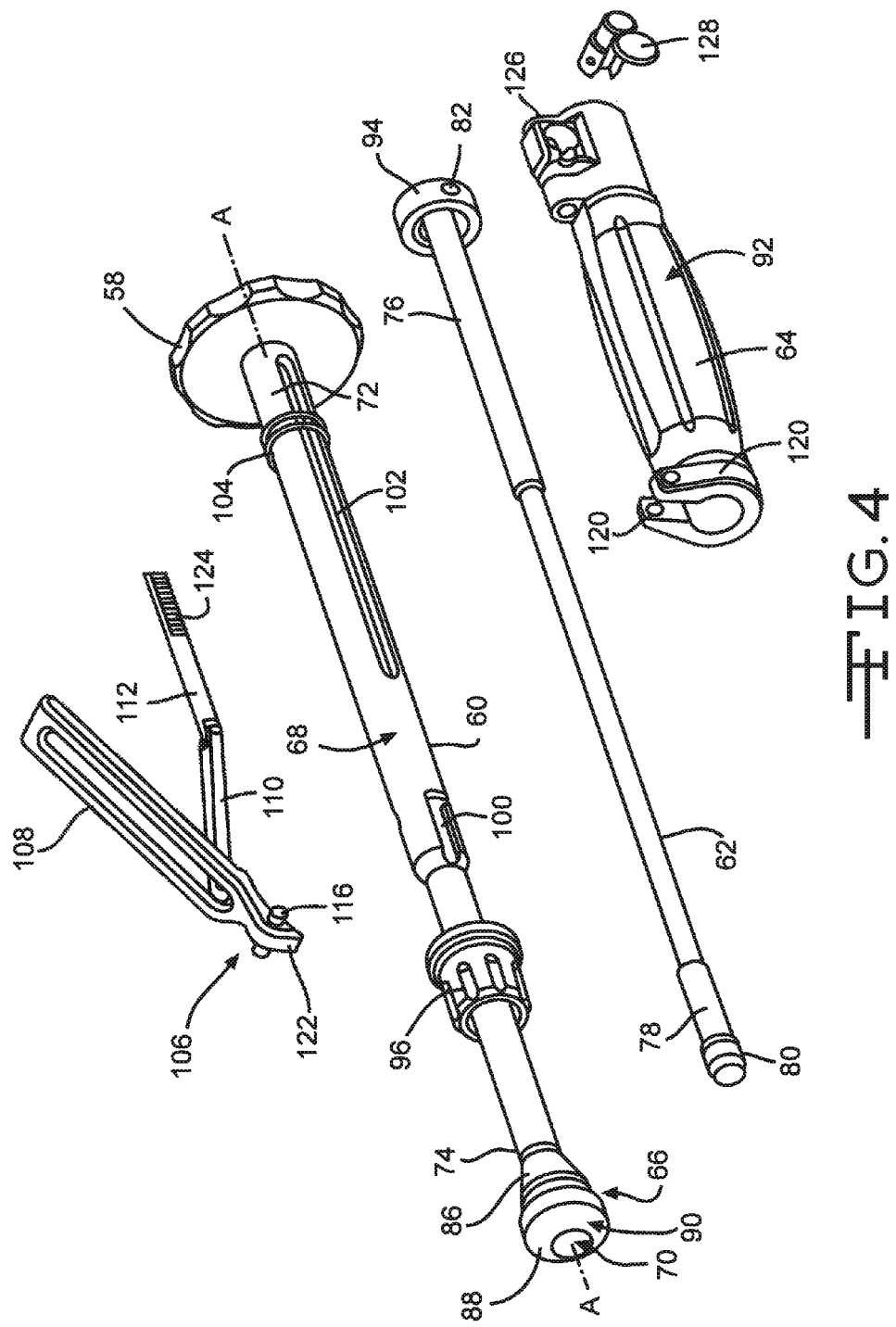
FIG. 4 is a perspective view of an embodiment of the components comprising the orthopedic impactor of the present invention.
Figure 5:
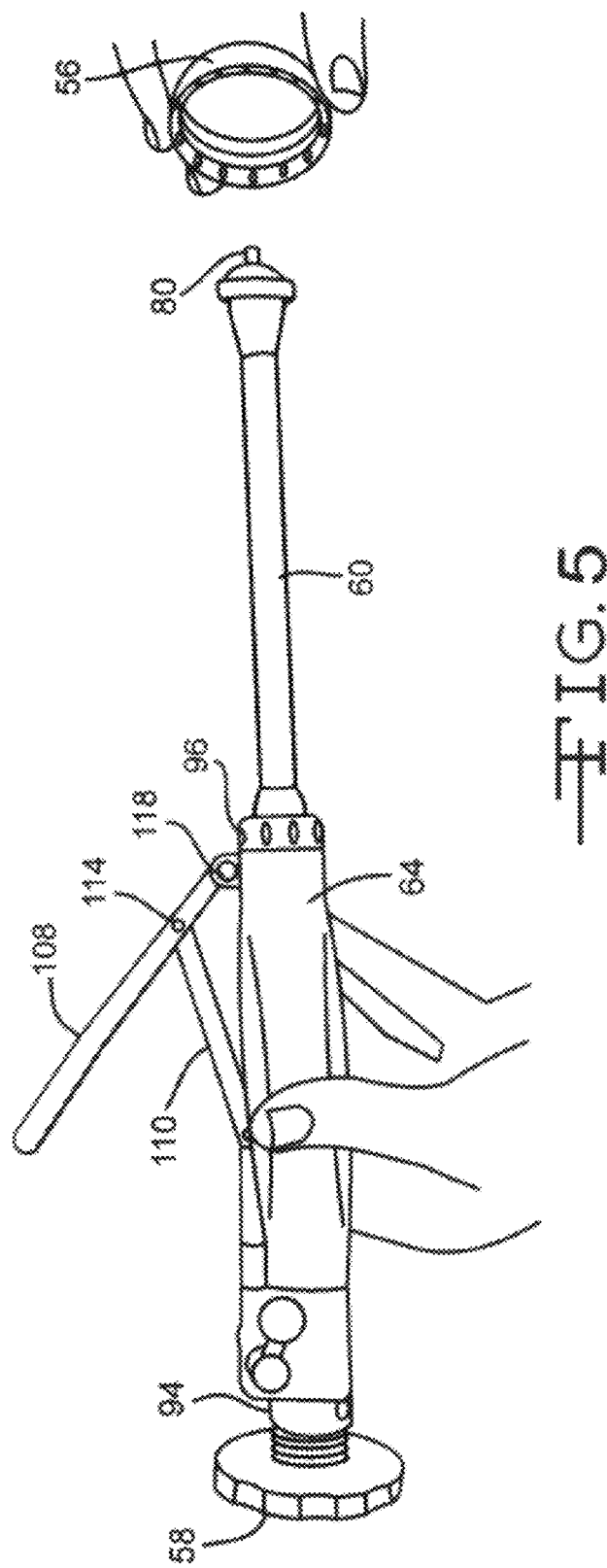
FIG. 5 illustrates a perspective view of an embodiment of an orthopedic prosthetic cup being attached to the impactor shown in FIG. 3.
Figure 6B:
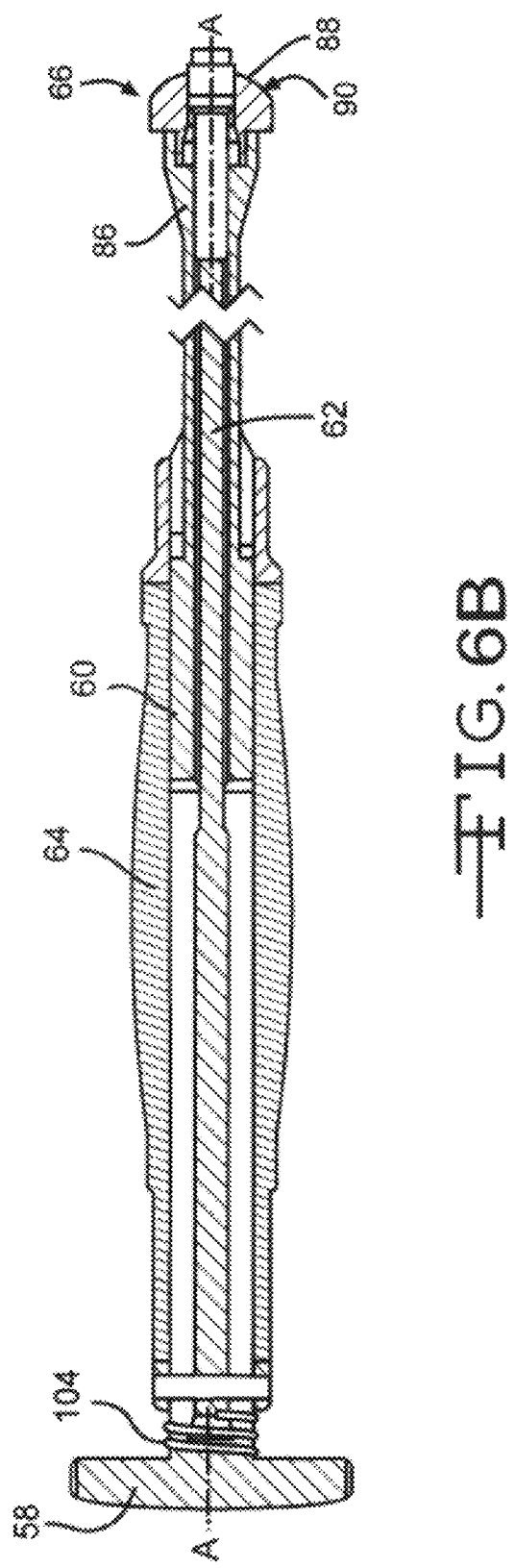
Figure 8D:
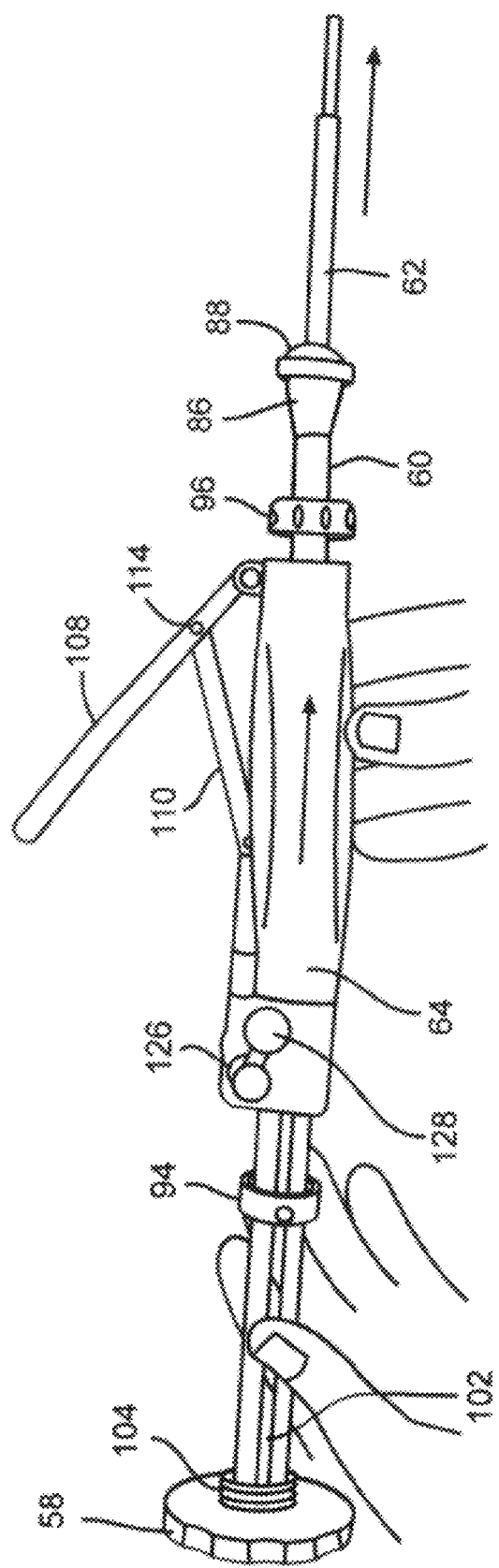

As shown in FIGS. 4 and 6-6B, the elongated body portion 60 has an internal cavity 70 that extends from a region of a body proximal end portion 72 through a distal end 74 of the body 60 along axis A-A. In a preferred embodiment, the body cavity 70 has a cylindrical shape with a generally circular cross-section providing a cavity diameter ranging from about 0.5 cm to about 4 cm. The cavity 70 may be constructed of a multitude of cross-sectional shapes that include but are not limited to, a rectangle, a square, a triangle, a hexagon, an oval, or the like.

The connection rod 62 has a rod proximal end portion 76 spaced apart from a rod distal end portion 78 with a rod length portion 80 residing therebetween. The connection rod 62 preferably positioned within the cavity 70 of the body 60 such that its proximal end portion resides within the proximal end portion of the body cavity 70. The distal end portion of the rod 62 protrudes from the distal end of the cavity 70. The rod 62 is constructed such that it is in a slidable relationship within the cavity 70.

The connection rod 62 has a length ranging from about 5 cm to about 50 cm and more preferably from about 10 cm to about 20 cm. The connection rod 62 has a circular cross-section. In a preferred embodiment, the rod 62 has a cross-sectional diameter ranging from about 0.5 cm to about 4 cm. Similar to the body portion 60, as previously described, the rod 62 may be constructed of a multitude of cross-sectional shapes that include but are not limited to, a rectangle, a square, a triangle, a hexagon, or an oval. In a preferred embodiment, the connection rod 62 may be constructed from metals comprising aluminum, stainless steel, cobalt nickel alloys, highly alloyed ferritic stainless steel containing molybdenum and chromium, and nickel-, chromium- and molybdenum-containing alloys and the like.

In a preferred embodiment, the distal end 78 of the rod 62 has a threaded end 80 that is design to engage with a threaded receiving end of the prosthetic cup 56. A throughbore opening 82 is positioned at the opposite, proximal end 76 of the rod 62. The throughbore opening 82 extends through the diameter of the rod, perpendicular to longitudinal axis A-A. The connection rod throughbore 82 allows for the placement of a connection rod pin 84. The pin is placed through the opening such that its opposing ends are in a perpendicular relationship to the longitudinal length of the rod 62. As will be discussed in more detail, this pin 84 and throughbore 82 feature of the rod 62 enable controlled movement of the rod 62 and cup 56.

As illustrated in FIGS. 3-5, 6-6B and 8B-8D, the prosthetic cup engagement portion 66 resides at the distal end 74 of the elongated body 60. The prosthetic cup engagement portion 66 comprises a frustro-conical portion 86 that fluidly transitions into an end cap portion 88. As shown, the frustro-conical portion 86 residing at the distal end of the body 60, has a wider diameter than the diameter of the body length portion. In a preferred embodiment, the end cap 88 has a curved outer surface 90. These features of the cup engagement portion 88 are designed to contact the contoured inner surface of the prosthetic cup 56. Furthermore, the wider outer surface of the end cap 88 provides an increased surface area. The greater surface area provided by the outer surface of the end cap portion 88 distributes the impaction force over a wider contact interface, therefore minimizing stress risers at the impactor 50 to prosthetic cup 56 connection point.

The strike plate 58 resides at the opposite, proximal end of the elongated body 60. The strike plate 58 is designed with a strike plate diameter that is wider than the outer diameter of the body 60. In a preferred embodiment, the diameter of the strike plate 58 ranges from about 2 cm to about 10 cm. As illustrated, the strike plate 58 is fluidly attached to the proximal end of the elongated body 60.

As shown in FIGS. 3, 5, 6-6B, and 8-8D, the handle portion 64 is positioned circumferentially around the outer diameter of the proximal end of the body 60. More specifically, the handle portion 64 is positioned circumferentially around the exterior of the annular sidewall 68 of the body 60. The handle portion 64 is designed such that it is in a slidable relationship with the sidewall 68 along axis A-A. In a preferred embodiment, the handle portion 64 has a generally tubular form. The handle portion 64 preferably has an inner handle diameter ranging from about 1 cm to about 3 cm. A ribbed gripping surface preferably comprises an outer handle surface 92.

In a preferred embodiment, a proximal ring 94 and a distal ring 96 are positioned adjacent respective proximal and distal ends of the handle portion 64. More specifically, the rings 94, 96 are positioned circumferentially around the exterior surface of the annular sidewall 68 of the body 62. In a preferred embodiment, the distal ring 96 and proximal ring 94 each have an outer diameter ranging from about 1 cm to about 5 cm and an inner diameter ranging from about 0.5 cm to about 4 cm.

Opposed distal ring positioning pins (not shown) extend from an inner surface of the distal ring 96. These positioning pins are designed such that they fit within geometrically opposed grooves 100 residing within a portion of the exterior surface of the annular sidewall 68 of the body 60. The grooves 100 are configured similar to that of a "dog leg" such that when the pins are received within the corresponding grooves 100 after the distal ring 96 has been rotated and locked into position with respect to the body 60. In a preferred embodiment, the groove is shaped similarly to that of the letter "J".

As shown in FIGS. 3, 5-5B, 6-6B, and 8-8D, the proximal ring 94 is positioned opposite the distal ring 96 and adjacent to the proximal end of the handle portion 64. The proximal ring 94 is preferably in a slidable relationship with the exterior surface of the sidewall 68 of the body 60 along longitudinal axis A-A.

As illustrated in FIGS. 4, 6-6B, and 8C-8D, the ends of the connection rod pin 84, extending through opposite sides of the connection rod 62, are positioned through respective slot openings 102 extending through opposing sides of the annular sidewall of the body 60. In a preferred embodiment, two opposing slot openings 102 extend through the annular sidewall of the proximal ring portion of the body 60. Each of the slot openings 102 has a distal and proximal slot portion and a slot length therebetween. The slots 102 are constructed such that they are contained within the boundaries of the annular sidewall of the body 60. More specifically, the proximal end portion of the slot is designed not to protrude through the proximal end 72 of the body 60. As shown in FIGS. 4, 6-6B, and 8B-8D, a portion of annular sidewall 68 separates the proximal end of the slot 102 and the proximal end of the elongated body 60. In a preferred embodiment, the length of the portion of annular sidewall 68 positioned between the proximal end of the slot 102 and the proximal end of the elongated body 60 ranges from about 0.5 cm to about 5 cm or from about 0.1% to about 5% of the length of the elongated body 60. This portion of sidewall 68 that separates the respective proximal ends of the slot 102 and body 60 prevents the proximal end of the connection rod 62 from contacting the body 60, therefore minimizing the transfer of the impaction force to the connection rod 62 and prosthetic cup 56 during the implantation procedure.

As shown, once the ends of the rod pin 84 extend through the sidewall slots 102, the ends are positioned through opposing throughbores of the proximal ring 94. More specifically, the ends of the pins 84 are positioned through opposing throughbores that extend through the annular sidewall of the proximal ring 94. Once the proximal ring 94, connection rod 62, and rod pin 84 of the impactor 50 are connected, longitudinal movement of the connection rod 62 is controlled through movement of the proximal ring 94. Thus, when the proximal ring 94 is slid along axis A-A of the elongated body, the rod 62 is correspondingly moved within the cavity 70 of the impactor body. Furthermore, when the prosthetic cup 56 is connected to the distal end of the impactor 50, the cup 56 is also correspondingly moved.

In a preferred embodiment, a spring 104 resides between the strike plate 58 and the proximal ring 94. More specifically, the spring 104 resides circumferentially around the exterior surface of the annular sidewall 68 of the body 60 between the strike plate 58 and the proximal end of the proximal ring 94. The spring 104 provides a bias force that enhances separation between the strike plate 58 and the proximal ring 94. More specifically, the spring 104 provides the bias force that separates the proximal ring 94 and proximal end of the connection rod 62 from the inner surface of the strike plate 58. Therefore, when the strike plate 58 is struck thereby providing an impaction force to the proximal end of the impactor 50, the transfer of impaction force to the proximal end of the rod 62 is minimized. The impactor 50 of the present invention is designed such that the majority of the impaction force is transferred through the annular sidewall 68 of the elongated body 60 and not the connection rod 62. As a result, the concentration of impaction forces at the distal end of the rod 62, which might damage the connected prosthetic cup 56, is reduced.

As shown in FIGS. 3-4, 5, 6-6B and 8-8D, a lever arm subassembly 106 is pivotally connected to the exterior surface of the handle portion 64. The lever arm subassembly 106 comprises a lever arm 108, an intermediate arm 110 and an end arm portion 112. In a preferred embodiment, the intermediate arm 110 is pivotally connected to the lever arm 108 and the end arm 112 is pivotally connected to the intermediate arm 110. A pivot pin 114 is placed through each of the connections, connecting the lever arm 108 to the intermediate arm 110 and the intermediate arm 110 to the end arm 112.

As illustrated in FIGS. 3-4, 5, 6-6B and 8-8D, a lever arm pivot pin 116 extends perpendicularly through a lever arm throughbore 118 and connects with a corresponding lever arm support portion 120 positioned at the distal end portion of the outer surface of the handle 64. As illustrated, the lever arm 108 preferably comprises a wedge portion 122 residing at its distal end. More specifically, the lever arm throughbore 118 extends perpendicularly through the wedge portion 122 of the lever arm 108. The wedge portion 122 of the lever arm 108 is further positioned such that the angled end of the wedge 122 is positionable between the distal ring 96 and the distal end of the handle portion 64.

The lever arm subassembly 106 is designed such that when the lever arm 108 is moved in a pivotable manner in a downward direction towards the exterior surface of the handle portion 64, the wedge portion 122 drives the distal end of the handle portion 64 away from the distal ring 96. More specifically, the distal end of the slanted wedge portion 122 is positioned between the distal ring 96 and the distal end of the handle portion 64, adjacent the lever arm support portion 120. As the lever arm 108 moves in the downward direction, the distal end of the wedge portion 122 is driven further between the distal ring 96 and the handle portion 64. As a result, the slanted surface and the body of the wedge portion 122, move the handle portion 64 in a proximal direction, along longitudinal axis A-A, against the spring 114 towards the strike plate 58. This motion, in turn, moves the proximal ring 94 in a proximal direction towards the strike plate 58, which in turn, moves the distal end 78 of the rod 62 within the cavity 70 of the body 60.

Therefore, when a prosthetic cup 56 is attached to the distal end 78 of the connection rod 62, proximal movement of the rod 62 pulls the cup 56 closer to the distal end of the elongated body 60 as shown in FIGS. 6, 6A and 6B. More specifically, the curved outer surface of the prosthetic cup engagement portion 66 contacts the inside surface of the prosthetic cup 56 and provides a secure fitting therebetween. In addition, the outer surface of the end cap 88 provides a larger surface area that distributes the impaction force. In a preferred embodiment, as illustrated in FIG. 5A, the prosthetic cup 56 is secured to the distal end of the impactor 50 through clockwise rotation of the strike plate 58. Accordingly, the impactor 50 is detached from the prosthetic cup through counter-clockwise rotation of the strike plate 58 shown in FIG. 8A.

Referring again to the lever arm subassembly 106, a ratchet post 124 provided at the proximal end of the end arm 112. The ratchet post 124 is designed with teeth that protrude from a portion of the outer surface of the post 124. In a preferred embodiment, the ratchet post 124 is received within a ratchet catch locking mechanism 126 located at the proximal end portion of the handle 64. Once the ratchet post is received within the mechanism, the corresponding ratchet teeth become entrapped therewithin, thus preventing sliding movement of the handle portion 64. Correspondingly, the sliding movement of the proximal ring 94 is also prevented since it is positioned between the handle portion 64 and the biasing force of the spring 114 at the strike plate end. The locking mechanism 126 is constructed such that when the lever arm 108 is depressed, the ratchet post 124 moves in a proximal direction within the locking mechanism thereby becoming entrapped therewithin.

The ratchet locking mechanism 126 comprises a release lever 128. When the release lever is depressed, the ratchet teeth become disengaged from the mechanism. The ratchet post 124 and corresponding ratchet locking mechanism 126 enable the lever arm 108 to be locked in multiple locations within the operating movement of the arm 108.

Although a threaded screw fitting is the preferred means of attachment of the prosthetic cup 56 to the impactor 50 of the present invention, other cup attachment means could also be used. For example, as illustrated in FIG. 7, a cup-and-socket 130 type mechanism may be used. In addition, the cup attachment mechanism may be adapted for a double mobility prosthetic cup utilizing an expandable dome mechanism as disclosed in U.S. patent application Ser. No. 12/694,524, which is assigned to the assignee of the present invention and incorporated herein by reference may be used. Furthermore, a grasping plate cup attachment mechanism 132 illustrated in FIG. 7A, disclosed in U.S. patent application Ser. No. 13/219,767, which is assigned to the assignee of the present invention and incorporated herein by reference may also be used as well.

Once the prosthetic cup 56 has been securely connected to the distal end of the impactor 50, the impactor and prosthetic cup assembly is inserted within the target area of the acetabulum. Once correctly positioned, a series of impaction forces are delivered to the proximal end of the strike plate 58 securing the cup 56 therewithin. After the cup 56 is secured within the acetabulum, the cup is removed from the end of the impactor 50. As shown in FIGS. 8 and 8A, the release lever 128 of the ratchet post locking mechanism 126 is depressed. This action disengages the ratchet post 124 from the locking mechanism 126 thereby enabling the lever arm 108 to move freely away from the external surface of the handle portion 64. The lever arm 108 is pivoted away from the exterior surface of the handle portion 64. This lever arm 108 movement distally extends the connector rod 62. The strike plate 58 is then rotated in a counter clockwise direction to disengage the prosthetic cup 56 from the connection rod 62 and the body of the impactor is removed from the patient.

After the prosthetic cup 56 is deployed, the impactor 50 of the present invention may be further disassembled for cleaning and disinfection. As illustrated, in FIGS. 8B-8D, the distal ring 96 is first disengaged from the "J" groove 100. After the distal ring 96 is disengaged, the distal ring 96 and handle portion 64 are able to be moved freely along axis A-A. As shown, the respective strike plate 58 and frusto-conical prosthetic cup engagement end 66 of the one-piece body 60 construction of the elongated body 60 prevent complete disassembly of the components comprising the impactor 50, i.e. the spring 114, the handle portion 64 and the proximal and distal rings 94, 96. Furthermore, the pivot attachment of the lever arm subassembly prevents its removal or disassembly from the impactor 50. These design features of the impactor of the present invention enable thorough cleaning of the tool while reducing the possibility of misplacing the components of the impactor.

Accordingly, the invention is not limited, except by the appended claims.

What is claimed is:
1. An orthopedic impactor,
comprising:
a) an elongated body comprising a body sidewall surrounding a body lumen extending along a longitudinal axis from a proximal body portion providing a strike plate to a distal body portion having an open distal body end;

b) a connection rod positioned in the body lumen and having a rod length extending from a proximal rod end positioned in the proximal body portion to a distal rod end extending out of the open distal body end, wherein the distal rod end is connectable to a prosthetic cup;

c) a handle positioned in a slidable relationship along the longitudinal axis on the body sidewall, the handle having a proximal handle portion spaced from a distal handle portion;

d) a distal member fixed in a non-movable position on the body sidewall at the distal body portion; and e) a proximal member connected to the proximal rod end in a slidable relationship on the body sidewall at the proximal body portion; and f) a lever arm comprising a distal lever arm portion having a distal lever arm wedge end abutting the fixed distal member, wherein the distal lever arm portion is pivotally connected to the distal handle portion at a location that is proximal of the lever arm wedge end;

g) wherein actuation of the lever arm from a first position spaced from the body to a second position closer toward the body than the first position causes the distal lever arm wedge end to wedge against the fixed distal member to thereby cause the pivotable connection between the lever arm and the handle to move the handle in a proximal direction along the body sidewall and the longitudinal axis, which consequently moves the proximal member along the body sidewall and the connected rod along the body lumen to thereby cause the distal rod end connectable to a prosthetic cup to move the cup proximally against the distal body end.

2. The orthopedic impactor claim 1 wherein a bias member is positioned circumferentially around the body sidewall between the strike plate and the proximal member movable along the body sidewall.

3. The orthopedic impactor of claim 1 wherein a rod pin, having opposing ends, is positioned perpendicular through a connection rod throughbore at the proximal rod end wherein the rod pin is slidable along a slot extending through the body sidewall.

4. The orthopedic impactor of claim 3 wherein opposing ends of the rod pin extend through opposed slots in the body sidewall.

5. The orthopedic impactor of claim 3 wherein a proximal end of the slot is spaced from the strike plate at the proximal body end.

6. The orthopedic impactor of claim 1 wherein the elongated body including the strike plate is of a one piece construction.

7. The orthopedic impactor of claim 1 wherein the distal body portion has a frustro-conical shape extending proximally from an end cap portion.

8. The orthopedic impactor of claim 7 wherein the end cap portion has a curved outer surface.

9. The orthopedic impactor of claim 1 wherein the distal member is a ring having opposing ring pins that engage within opposed distal locking grooves residing in an outer surface of the body sidewall.

10. The orthopedic impactor of claim 9 wherein the locking grooves are J-shaped.

11. The orthopedic imapactor of claim 1 wherein the distal rod end is threaded.

12. The orthopedic impactor of claim 1 further comprising an intermediate arm extending from a proximal intermediate arm end to a distal intermediate arm end pivotably connected to the lever arm at a location that is proximal of the distal lever arm wedge end, and an end arm extending from a distal end arm portion pivotably connected to the proximal intermediate arm portion to a proximal end arm portion.

13. The orthopedic impactor of claim 12 wherein the proximal end arm portion comprises a ratchet post, the ratchet post receivable within a ratchet locking mechanism supported on the body sidewall and comprising a release lever.

14. The orthopedic impactor of claim 1 wherein the prosthetic cup engagement portion comprises a cup-and-socket mechanism, an expandable dome mechanism, or a grasping plate mechanism.

15. The orthopedic impactor of claim 1 wherein the distal member is a distal ring and the proximal member is a proximal ring, both supported on the body sidewall.

16. A method of inserting a prosthetic cup within the acetabulum, the method comprising:

a) providing an orthopedic impactor comprising:
  i) an elongated body extending along a longitudinal axis, a strike plate located at a body proximal end portion spaced apart from a prosthetic cup engagement portion located at a body distal end portion, an annular sidewall therebetween, and a body cavity residing therewithin extending from the proximal end portion through the distal end portion;
  ii) a handle portion having a handle proximal end spaced from a handle distal end residing along a body annular sidewall outer surface, the handle portion positioned in a slidable relationship along the longitudinal axis between a distal ring and a proximal ring that circumferentially extend around the body annular sidewall;
  iii) a connection rod having a rod proximal end spaced from a rod distal end positioned within the body cavity; and
  iv) a lever arm comprising a distal wedge portion, pivotally connected to the handle portion, the wedge portion positionable between the distal ring and the handle distal end;

b) connecting an orthopedic prosthetic cup to the connection rod distal end;

c) depressing the lever arm such that the lever arm moves towards a handle outer surface driving the wedge portion between the handle distal end and the distal ring and securing the orthopedic prosthetic cup to the prosthetic cup engagement portion;

d) inserting the impactor within the acetabulum;

e) applying an impaction force to the strike plate;

f) releasing the orthopedic prosthetic cup from the impactor; and g) removing the impactor from the acetabulum.

17. The method. of claim 16 including providing a bias member positioned circumferentially around the body annular sidewall between the strike plate and the proximal ring.

18. The method of claim 16 including providing a rod pin, having opposing ends, positioned perpendicularly through a rod throughbore, the throughbore residing at the proximal end of the rod, wherein the rod pin extends through a body annular sidewall slot.

19. The method of claim 18 wherein the opposing ends of the rod pin extend through a proximal ring annular sidewall.

20. The method of claim 18 wherein a portion of the elongated body sidewall separates a slot proximal end from the body proximal end.

21. The method of claim 16 wherein the prosthetic cup engagement portion comprises a cup-and-socket mechanism, an expandable dome mechanism, or a grasping plate mechanism.

22. An orthopedic impactor, comprising:
a) an elongated body comprising a body sidewall surrounding a body lumen extending along a longitudinal axis from a proximal body portion providing a strike plate to a distal body portion having an open distal body end;
b) a connection rod positioned in the body lumen and having a rod length extending from a proximal rod end positioned in the proximal body portion to a distal rod end extending out of the open distal body end, wherein the distal rod end is connectable to a prosthetic cup;
c) a handle positioned in a slidable relationship along the longitudinal axis on the body sidewall, the handle having a proximal handle portion spaced from a distal handle portion;
d) a distal member fixed in a non-movable position on the body sidewall at the distal body portion; and
e) a proximal member connected to the proximal rod end in a slidable relationship on the body sidewall at the proximal body portion;
f) a bias member positioned circumferentially around the body sidewall between the strike plate and the proximal member;
g) a lever arm comprising a distal lever arm portion having a distal lever arm wedge end abutting the fixed distal member, wherein the distal lever arm portion is pivotally connected to the distal handle portion at a location that is proximal of the lever arm wedge end, and the lever arm pivotally connected to a distal end intermediate arm portion, a proximal end intermediate arm portion pivotally connected to a distal end arm portion;
h) wherein actuation of the lever arm from a first position spaced from the body to a second position closer toward the body than the first position causes the distal lever arm wedge end to wedge against the fixed distal member to thereby cause the pivotable connection between the lever arm and the handle to move the handle in a proximal direction along the body sidewall and the longitudinal axis, which consequently moves the proximal member along the body sidewall and the connected rod along the body lumen to thereby cause the distal rod end connectable to a prosthetic cup to move the cup proximally against the distal body end; and
i) wherein actuation of the lever arm from the first position spaced from the body to the second position closer toward the body causes the proximal end intermediate arm portion to move in a proximal direction toward the strike plate, which in turn causes a proximal, end arm portion to move in a proximal direction, receivable within a ratchet locking mechanism comprising a release lever.

23. The orthopedic impactor of claim 22 wherein the proximal end arm portion comprises a ratchet post receivable within a ratchet locking mechanism opening.

24. The orthopedic impactor of claim 22 wherein a rod pin, having opposing ends, is positioned perpendicularly through a connection rod throughbore, the throughbore residing at the rod proximal end, wherein the rod pin is positioned through a slot extending through the body sidewall.

25. The orthopedic impactor of claim 22 wherein the elongated body including the strike plate is of a one piece construction.

26. The orthopedic impactor of claim 22 wherein the prosthetic cup engagement portion comprises a cup-and-socket mechanism, an expandable dome mechanism, or a grasping plate mechanism.

* * * * *

UNITED STATES PATENT AND TRADEMARK OFFICE
CERTIFICATE OF CORRECTION

PATENT NO.        : 8,585,709 B2
APPLICATION NO.   : 13/351302
DATED             : November 19, 2013
INVENTOR(S)       : Jonas Burgi Page 1 of 1

It is certified that error appears in the above-identified patent and that said Letters Patent is hereby corrected as shown below:

In the Claims

Column 9, line 40, (Claim 3, line 3) after the words "rod end" insert --,--

Column 9, line 63, (Claim 11, line 1) delete "imapactor" and insert --impactor--

Signed and Sealed this
Twenty-fourth Day of June, 2014

Michelle K. Lee
*Deputy Director of the United States Patent and Trademark Office*